(12) United States Patent
Liebholz et al.

(10) Patent No.: US 7,029,852 B2
(45) Date of Patent: *Apr. 18, 2006

(54) APPARATUS AND METHOD FOR DETECTING AND CLASSIFYING CHEMICALS, PARTICLES, VIRA, AND BACTERIA IN FLUIDS

(76) Inventors: Stephen W. Liebholz, 1204 Pheasant Rd., Rydel, PA (US) 19046; John Maniello, 9 Island Ave., 801, Miami Beach, FL (US) 33139

( * ) Notice: Subject to any disclaimer, the term of this patent is extended or adjusted under 35 U.S.C. 154(b) by 275 days.

This patent is subject to a terminal disclaimer.

(21) Appl. No.: 10/190,894

(22) Filed: Jul. 8, 2002

(65) Prior Publication Data

US 2004/0029183 A1 Feb. 12, 2004

Related U.S. Application Data

(63) Continuation of application No. PCT/US01/21820, filed on Jul. 11, 2001, and a continuation-in-part of application No. 09/613,942, filed on Jul. 11, 2000, now abandoned.

(51) Int. Cl.
*C12Q 1/68* (2006.01)

(52) U.S. Cl. .............................. 435/6; 422/101; 95/268; 55/326; 55/434; 73/1.06; 73/863; 435/7.1; 435/174; 435/287.1; 436/172

(58) Field of Classification Search ................ 210/634, 210/645, 650, 651, 263, 348; 435/4, 6, 7.1, 435/7.2, 7.31, 7.9, 7.92, 8, 29, 174, 287.1; 436/63, 164, 172, 174, 800, 805, 807, 824; 422/101; 95/267–268; 55/326, 424; 73/1.06, 73/863

See application file for complete search history.

(56) References Cited

U.S. PATENT DOCUMENTS 5,290,707 A 3/1994 Wood (Continued)

FOREIGN PATENT DOCUMENTS

| WO | WO 99/27351 | 6/1999 |
| WO | WO 01/32911 A2 | 5/2001 |

OTHER PUBLICATIONS

Romanova et al, Bioluminescence of Free and Poly(vinyl alcohol) Cryogel-Entrapped recombinant *Escherichia coli* Cells Expressing Firefly Lusiferase, Biochemistry (Moscow), vol. 63, No. 5, 1998, pp. 579-583.

1998 Army Science and Technology Master Plan, Chapter III K. Niclear, Biological, and Chemical, http://www.sarda.army.mil/sard-zt/ASTMP98/vol-i/sec3/sec3k.htm.

*Primary Examiner*—Long V. Le
*Assistant Examiner*—Christine Foster
(74) *Attorney, Agent, or Firm*—Roberts, Abokhair & Mardula, LLC

(57) ABSTRACT

The present invention is drawn to the detection of harmful agents, known or previously unknown, using a biosensor. The biosensor makes use of non-living biological or biochemical sensor molecules for detecting and classifying chemicals, poisons, particles, vira, and bacteria in fluids. In a preferred embodiment, the bioreceptor comprises sensor molecules packaged in a collection device and treated to evoke an optical response to the presence of harmful agents, allowing for photocell detection and signal processing. The sensor molecules are selected from the group of biological molecules consisting of aptamers, single-chain nucleic acids, double-chain nucleic acids, hybridized chemicals incorporating these molecules and combinations thereof that bind with harmful agents. The harmful agents can also be collected in this manner for further analysis, and antibodies produced by the apparatus.

11 Claims, 8 Drawing Sheets

U.S. PATENT DOCUMENTS 5,526,685 A        6/1996    Davis
5,841,037 A  *   11/1998   Ulfik et al. .................... 73/863
6,051,388 A        4/2000    Bodenhamer
6,087,114 A        7/2000    Rider
6,090,545 A  *    7/2000    Wohlstadter et al. .......... 435/6
6,105,440 A        8/2000    Lawless
6,478,856 B1 *  11/2002   Leibholz et al. .............. 95/268

* cited by examiner

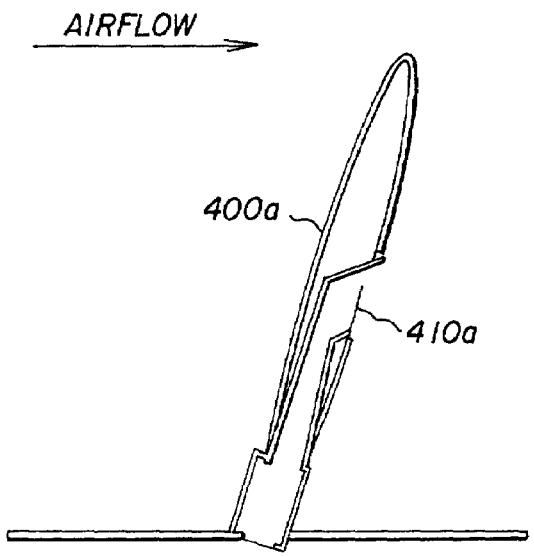
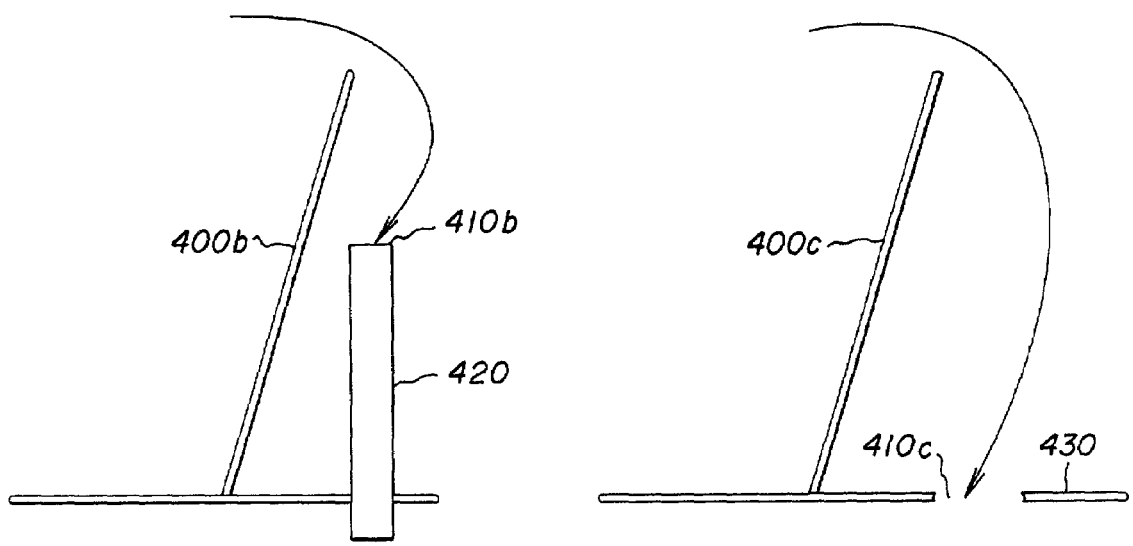
Fig. 4a
Fig. 4b
Fig. 4c

APPARATUS AND METHOD FOR DETECTING AND CLASSIFYING CHEMICALS, PARTICLES, VIRA, AND BACTERIA IN FLUIDS

RELATIONSHIP TO PRIOR APPLICATIONS

This application is a continuation of and claims priority under 35 U.S.C § 120 and § 365(a) to PCT Application No. PCT/US01/21820, filed Jul. 11, 2001 and is a continuation-in part of U.S. application Ser. No. 09/613,942, filed Jul. 11, 2000, now abandoned.

FIELD OF THE INVENTION

The present invention is drawn to the detection of harmful agents, or agents in general, using a non-living biosensor. More particularly, it is drawn to the use of aptameric and related bioreceptors for detecting and classifying chemicals, poisons, particles, vira, and bacteria in fluids. In a preferred embodiment, a bioreceptor, selected from the group consisting of aptameric compounds, nucleic acids (i.e., single-chain and double-chain), hybridized chemicals incorporating these molecules and combinations thereof, is packaged in a collection device and treated to evoke an optical response to the presence of such agents, allowing for photocell detection and subsequent optional signal processing. These agents can also be collected in this manner for further analysis.

BACKGROUND INFORMATION

Chemical and biological weapons, sometimes referred to as the "poor man's nuclear weapons," pose a significant threat in the post-Cold War environment. The relative low cost and simplicity of their design and technology, in comparison to nuclear weapons, make them the weapons of mass destruction choice for a variety of rogue states and terrorist, non-state organizations. This threat has been made all the more tangible by the use of chemical agent in a Tokyo subway, and allegations over Iraq's development of chemical and biological weapons and its actual use of chemical weapons in combat operations.

More recently, the use of anthrax-tainted letters through the mail and the revelation of an al-Qaeda plot to explode a radioactive "dirty bomb" have made the threat real to the U.S. homeland.

According to the 1998 U.S Army Science and Technology Master Plan, "New fluorescent, acoustic, and optical biosensors are being designed for enhanced sensitivity and more flexible detection capability. Recent advances in the acceleration of the polymerase chain reaction (PCR) on a miniaturized scale now permit the exploitation of DNA probes for field detection of pathogens. A major thrust of a *Joint Warfighting Science and Technology Plan* (JWSTP) Defense Technology Objective (DTO), J.04 "Integrated Detection Advanced Technology Demonstration (ATD)," is the development of a rapid, automated field detection device based on the PCR. One key DTO element is the development of recombinant antibodies to serve as the recognition element of these new biosensors (FY98). Recombinant antibodies will ultimately be designed and quickly selected from genetic "super libraries" (FY99) to have specific detection capabilities, and novel starburst dendrimers are being studied for use on tailored reactive surfaces. Another major approach to point detection is mass spectrometry (MS), and miniature automated pyrolysis-based versions are being assessed for integration into existing CBD platforms (FY01). Of critical importance for biosensor and MS approaches is bio-aerosol sampling, since characteristics (e.g., concentration of detectable units per unit volume of air) of biological aerosols differ dramatically from chemical vapors, with resulting effects on detection efficacy."

U.S. Pat. No. 6,087,114 to Rider discloses an optoelectronic sensor that uses B-cells to detect antigens, but the sensor has limited deployment capabilities since it requires a liquid medium with nutrients to maintain the metabolic requirements of the cell.

Of particular concern, which this invention addresses, are needs for (1) detecting, classifying and capturing agents heretofore undiscovered or unanalyzed, (2) annunciating these findings with a typical total processing time from exposure of about one second, (3) compactness and relatively low cost combined with long unattended life in the field, and (4) sensitivity to agents whose lethal or otherwise effective concentration in the environment will be extremely low compared to the comparable prior art.

BRIEF SUMMARY OF THE INVENTION

It is an object of the invention to use aptameric compounds, nucleic acids (single and double strand) and hybridizations incorporating similar molecules and combinations thereof for detecting and classifying chemicals, particles, vira, and bacteria in fluids.

It is yet another object of the invention to provide a system for directing harmful agents onto a sensor surface for use in detecting and classifying chemicals, particles, vira, and bacteria in fluids.

It is yet another object of the invention to provide diagnostic information and annunciation, either locally or remotely, within approximately 1 second or less of exposure to an agent in the free fluid, the time being short enough to become a function of the biochemical sensing apparatus alone.

It is another object of the invention to provide a compound of the present invention packaged in a collection device and treated to evoke an optical response to the presence of harmful agents, allowing for photocell detection and/or collection of the harmful agents.

It is an object of the invention to provide a biosensor having a structure for sorting and selecting components of a fluid for acquisition and impingement on sensor surfaces for alarm and/or analysis purposes.

It is an object of the invention to use a bioreceptor selected from the group consisting of aptamers, single-chain nucleic acids, double-chain nucleic acids, hybridized chemicals incorporating these molecules, and combinations thereof for the detection of harmful agents.

It is another object of the invention to provide the functions of acquisition, filtering, sorting, selection, impingement on sensor surfaces and trapping of particles in a fluid, in accordance with desired mathematical functions of size, density, shape and surface characteristics.

It is another object of the invention to provide a combination of mechanical, aerodynamic, and kinetic methods to concentrate and/or sort particles of desired size and/or density from a fluid (gaseous, vapor or liquid) for detection by a sensor.

It is another object of the invention to provide a combination of mechanical, aerodynamic, and kinetic methods to impinge particles of desired size and/or density onto a bioreceptor surface for detection.

It is another object of the invention to provide a system for providing rapid annunciation of chemical, biological, and nuclear threats through interconnection of a plurality of biosensors via a central readout and decision system.

It is yet another object of the invention to provide a biosensor using aptamers, single-chain nucleic acids, double-chain nucleic acids, hybridized chemicals incorporating these molecules, or combinations thereof for the detection of harmful agents.

It is another object of this invention to provide broad annunciation capability combined with specificity, against agents that may not yet have been discovered by the emplacer of the biosensor It is another object of this invention to achieve a sensing and processing time of about one second from exposure.

It is another object of this invention to combine compactness and low cost with long unattended life in the field. By using sensor molecules instead of living cells, the present invention eliminates the metabolic requirements associated with a cell-based sensor such as found in U.S. Pat. No. 6,087,114 to Rider.

It is another object of this invention to provide sensitivity to agents at very low concentrations in the environment.

It is a further object of this invention to provide for capturing the offending agents and furnishing a means for rapid preparation of antibodies to these agents.

BRIEF DESCRIPTION OF THE DRAWINGS

FIGS. 4a–4c disclose isokinetic separators used in the present invention.

DETAILED DESCRIPTION OF THE INVENTION

The present invention is to method and apparatus for directing harmful agents onto a non-living bioreceptor surface for use in detecting and classifying chemicals, poisons, particles, vira, and bacteria in fluids, herein collectively referred to as agents. As used herein, the term bioreceptor refers to a substrate containing a set of chosen sensor molecules. As used herein, the term fluid is intended to comprise, without limitation, any fluid including air and water, or fluids used as intermediates to convey agents to the device from solid objects or surfaces.

The present invention incorporates a sensor for biological pathogens and poisons, chemical poisons, including neurotoxins and metabolic poisons, and drug or weapon precursor chemicals in the air or other fluids. The sensor is based on an aptamer, single-chain nucleic acid, double-chain nucleic acid, hybridized chemical incorporating these molecules, or combinations thereof. The sensor is treated with fluorescent or luminescent dye to evoke an optical response to a change in electrical potential. The sensor is selected and/or trained to respond to selected antagonists and ignore others.

In a preferred embodiment, the bioreceptor is an aptamer on a suitable organic substrate, optionally protected by a barrier or filter that is porous to aerosols, particles and spores of a desired diameter and to gases dissolved in the in the atmosphere. Glass is a preferred substrate, although certain plastics may also be desirable due to the possibility allowing a greater number of active sensor molecule sites per unit area. A suitable barrier can be formed as a membrane or filter and can be applied at the intake, outlet, or covering the wells of the sensitive region. One suitable material for the optional barrier is polytetrafluoroethylene (PTFE) film with perforations of approximately 10 μm in diameter. In one embodiment, particles>10 μm are meghanically and/or aerodynamically filtered out.

The aptamer, single-chain nucleic acid, double-chain nucleic acid, hybridized chemical incorporating these molecules, or combinations thereof chosen and/or synthesized and/or trained for this task should have certain properties discussed below.

The term trained refers to any method for selecting or controlling the receptors of that aptamer, single-chain nucleic acid, double-chain nucleic acid, hybridized chemical incorporating these molecules, or combinations thereof to bind with desired agents. Their included properties should:

- have minimal changes in sensor characteristics due to temperature, pressure or humidity changes
- respond to desired challenges and not respond to other challenges in selected patterns of response/non-response
- provide optical (including fluorescent and/or luminescent) indication or readout of activation, optionally incorporating both space-dependent and time-dependent signaling characteristics
- provide optical (including fluorescent and/or luminescent) readout of activation including space-dependent and/or time-dependent processing of the readout data as detection and classification variables
- possess minimum sensitivity to temperature variations
- provide response to classes of challenges not previously catalogued and/or for which specific antibodies, DNA sequences or protein sequences may have or have not been determined
- provide conversion of changes in electrical potential to photons via luminescent or fluorescent means for the purpose of producing a readout of response to viral, bacterial or chemical challenges of selected or broad natures, and
- provide means for generating antibodies to collected agents within the apparatus.

The biosensor of the present invention may incorporate Aristotelian and/or Non-Aristotelian logic, including multi-valued logic and statistical estimation to provide diagnostic information incorporating resistance to deliberately induced or accidental false alarms.

Each sensor may contain a replaceable plate or cartridge for holding the sensor molecules, with the number of containers dependent on the deployed embodiment, such as in a rectangular or hexagonal configuration, with outlet holes for the air or other fluid interspersed among the sensor molecules in the plate.

The biosensor container is generally in the form of a non-spherical optics subsystem and container, with reflective and/or refractive means to concentrate emitted photons to a small region external to the container. Each container terminates in a conventional photocell that collects the emitted photons resulting from activation of the sensor molecules, either via luminescent response, such as, but not limited to, infused luciferase or aequorin, or via fluorescent response to infrared, ultraviolet or visual light stimulated emission. The collected photons are then converted to electrons by conventional photocell means and processed in a known manner to elicit space-time characteristics of the response. The results, incorporating both space-time characteristics of pattern response to activation of bioreceptors in individual containers, and the pattern of containers activated, are processed via appropriate Aristotelian and non-Aristotelian (probabilistic) logic to yield diagnostic signals.

Preferably, the challenging substance is also collected in the sensor package for further analysis. Additionally, the invention includes but is not limited to the use of shutters or trapdoors to control which bioreceptor containers are available to activation at a given time.

The invention includes the feasibility of rapid generation of antibodies using the device and captured samples, after exposure.

Figure 1:
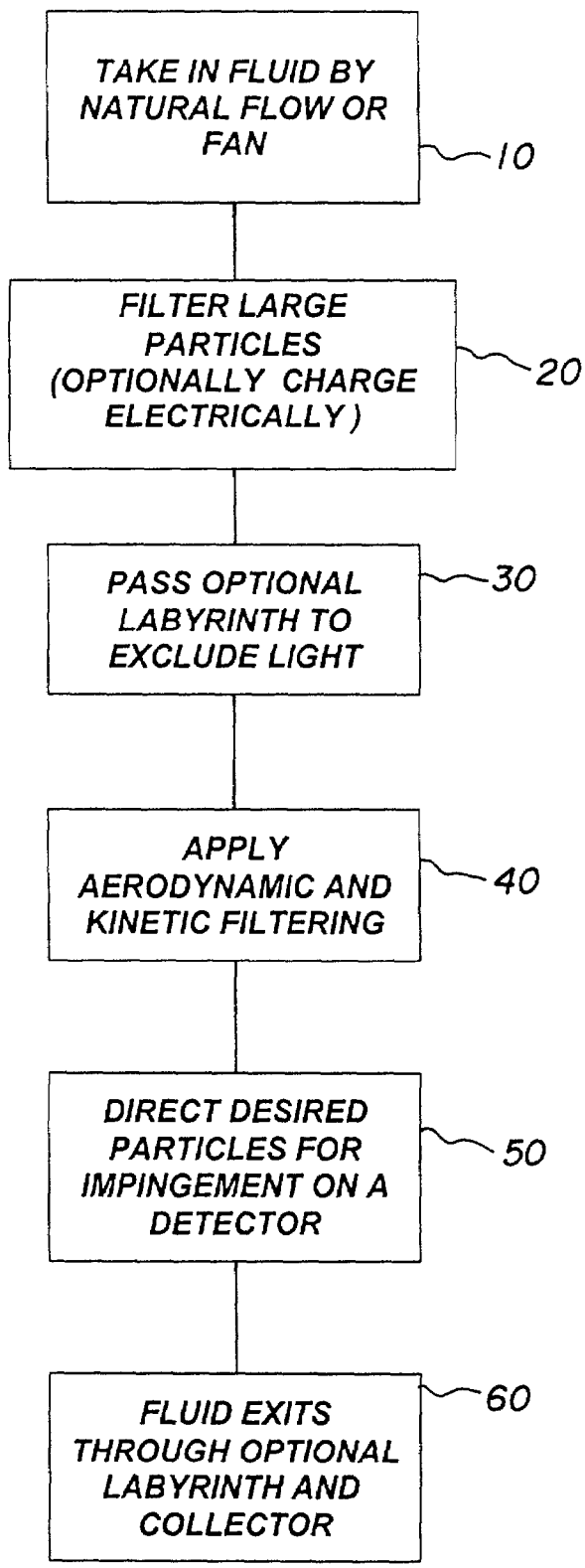
FIG. 1 discloses a basic schematic of the present invention.

In its most basic form, as shown in FIG. 1, the present invention provides a means to concentrate and impinge particles, spores, vapors, and gasses from air or another fluid medium onto the bioreceptor. The fluid is taken in either through natural stream flows or via a small fan as shown at 10, and passed through a filter designed to remove large particles from the fluid as shown at 20, which may also incorporate the barrier discussed above. The resulting flow is then introduced into a chamber after optionally being electromagnetically charged and directed.

The impingement includes, without limitation, presenting pathogenic organisms, whether or not incorporated in aerosols, and/or toxins and poisons (including "poison gas" agents) suspended in the fluid as aerosols, vapors, gases, solutions, particles or by other means, onto sensitive surfaces of the bioreceptor intended to process the material, as shown at 50.

The chamber consists of a series of collectors at one end, interspersed with one or more exit orifices. An optional sinusoidal or otherwise varying electrical field designed to optimally control the motion of the particles within the chamber sets up electrodynamic forces that cause the collectors, which are part of the electrodynamic apparatus, to attract the agents being collected and/or tested. This mechanism is discussed further below. The motion of the particles is generally in the form of a nonlinear vector motion and/or, but not limited to, a wave of increasing amplitude, terminating in impingement on the bioreceptor surface.

The remaining components of the fluid exit the chamber, and optionally pass through a finer filter to provide additional collection means.

The sensitive structure consists of a plate, volumetric receiver or array or other array of one or more sensitive bioreceptors of the present invention, each of which, provides one or more components of the analysis that the entire system is assigned to accomplish.

The fluid passage optionally contains a series of designed bends or labyrinth, as shown at 30 whose purpose is to block light from the sensitive materials, as well as providing a portion of the aerodynamic filtering. This is in addition to the conventional mechanical filtering cited above.

The aerodynamic and kinetic filtering of 40 consists of one or more of three components. First, the bends in the passage are designed to employ a balance of centrifugal and drag forces to select out particles whose ratio of radius-squared to total mass (i.e. density times radius-cubed times four-thirds Pi) meets desired characteristics, mediated by the deliberately variable airflow in the bent section. Other mathematical functions serving as criteria for forting and selection include Bernoulli forces, and the effects of Reynolds and Froude Numbers as examples.

A structure bearing an aerodynamic functional resemblance to the Turbinate bone of vertebrate animals (found elsewhere in Nature as well) is optionally utilized to assure proper randomization of the components, as well as to cause early non-sensitive impingement of particles of undesired effective (i.e. aerodynamic) diameters.

In the preferred embodiment the optimum particle size for impingement is matched to the alveolar capture function, described below.

Each sensitive detector is optionally covered with a small trapdoor which when closed by electrical or mechanical means seals an associated detector. When open, the trapdoor optionally erects to a critical angle obtuse to the fluid stream, providing further optional selection of components of the stream using laminar or turbulent vortices to further provide discrimination for particle size and density.

The optional electromagnetic component of the device consists of a varying electrostatic field with incidental magnetic field optimized to accelerate particles of the appropriate size (surface area) and density onto the sensitive surface. The field either utilizes the induced dipole component of the particles being sorted or selected, or makes use of an electrostatic monopole on the each of the particles, using traditional methods for inducing the electrostatic monopole.

The fluid exits from the chamber (i.e., the chamber containing the plate or array and associated components) through holes in the plate or array interspersed among the detectors. The fluid then optionally passes through another light-restricting labyrinth to the exit and optional collection filter as shown at 60.

In a preferred embodiment of the present invention, for combining with a sensor, the system has the responsibility of:

(1) extracting desired aerosol, vapor, gases and solid particles from the air,
(2) eliminating particles of inappropriate size (e.g., dust on one end and smoke on the other),
(3) sorting these particles while preserving viability of carried organisms, and
(4) concentrating and impinging the desired particles on the sensitive surface of the sensor.

The system can be broken down into four subsystems, not precisely corresponding to the above functions. It is optimized for acquisition of particles (aerosol or solid) forming particular mammalian threats, i.e. nominally 1–5 μm in mean diameter.

Figure 2:
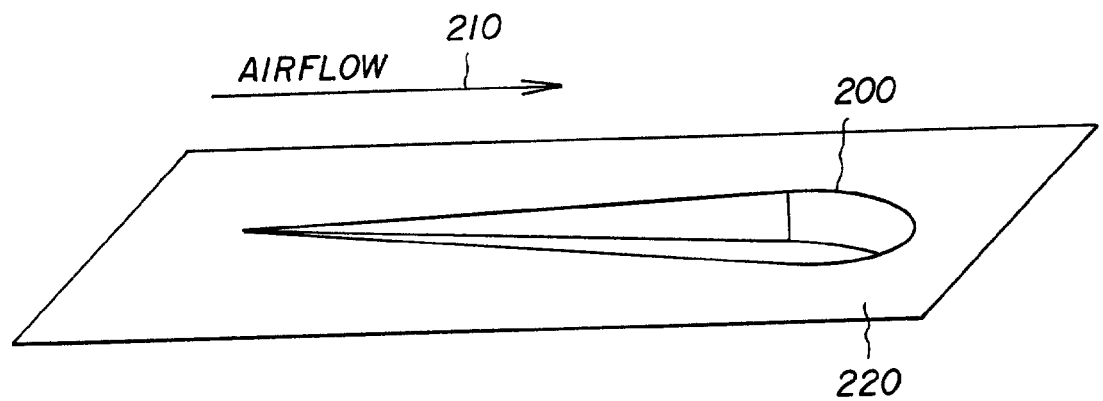
FIG. 2 discloses a preferred intake port for the present invention.

The first subsystem is concerned with particle acquisition and large-particle sorting. The challenge is that of capturing valid air samples despite wind direction and velocity. For this task the present invention preferably uses an omnidirectional assembly of the NACA flush intake design used in low-speed aircraft, which has the advantage of providing a positive Bernoulli-derived pressure to assure that sampling takes place. This has the further advantage of minimizing rain and small-particle effects, which could have an undesired effect on a sensor package. One such flush intake is diagramed in FIG. 2 in which fluid such as airflow 210 is taken into NACA intake 200 in plate 220. One such duct is of course partially unidirectional.

Figure 3:
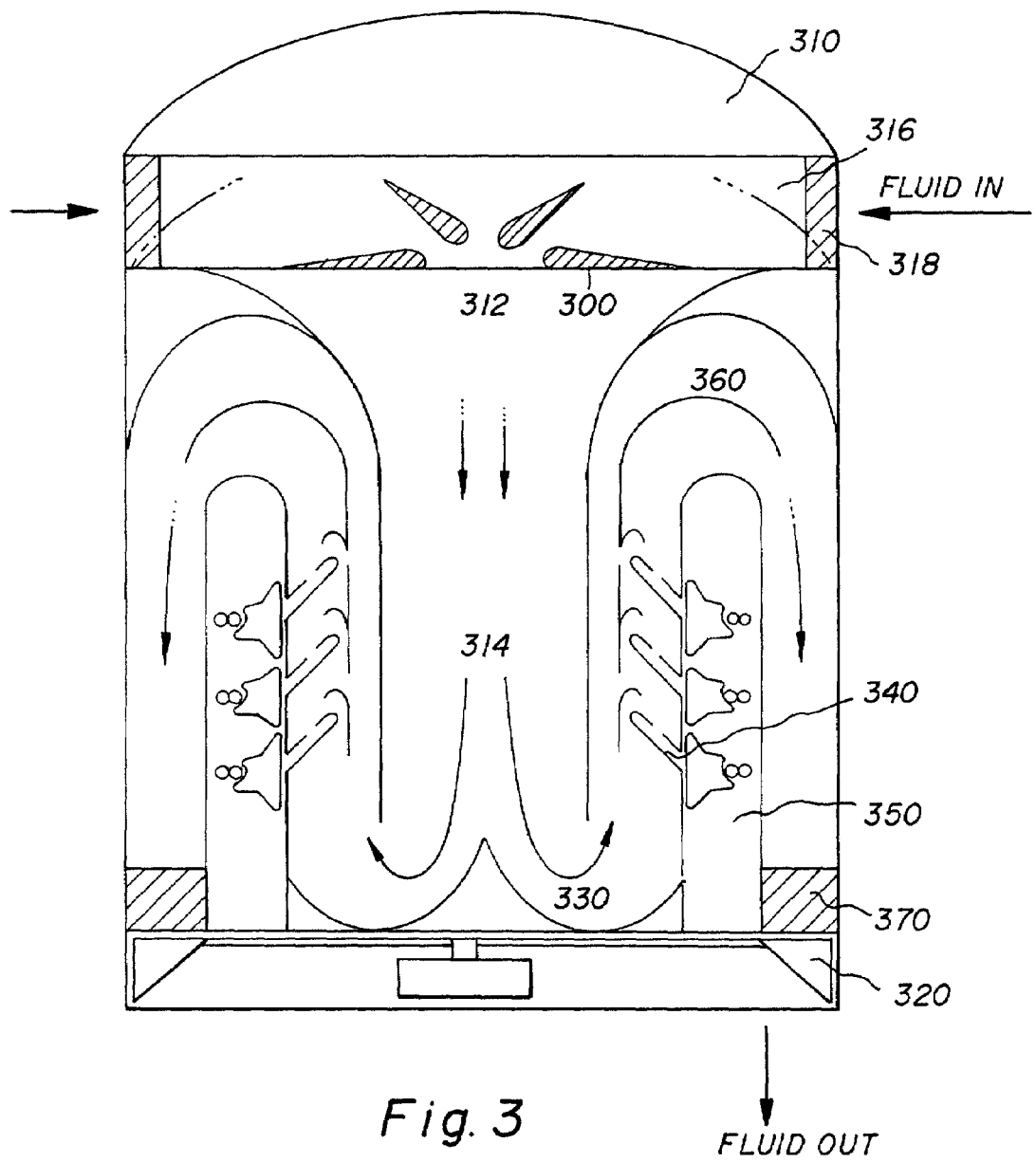
FIG. 3 discloses a preferred embodiment of the present invention.
Figure 5:
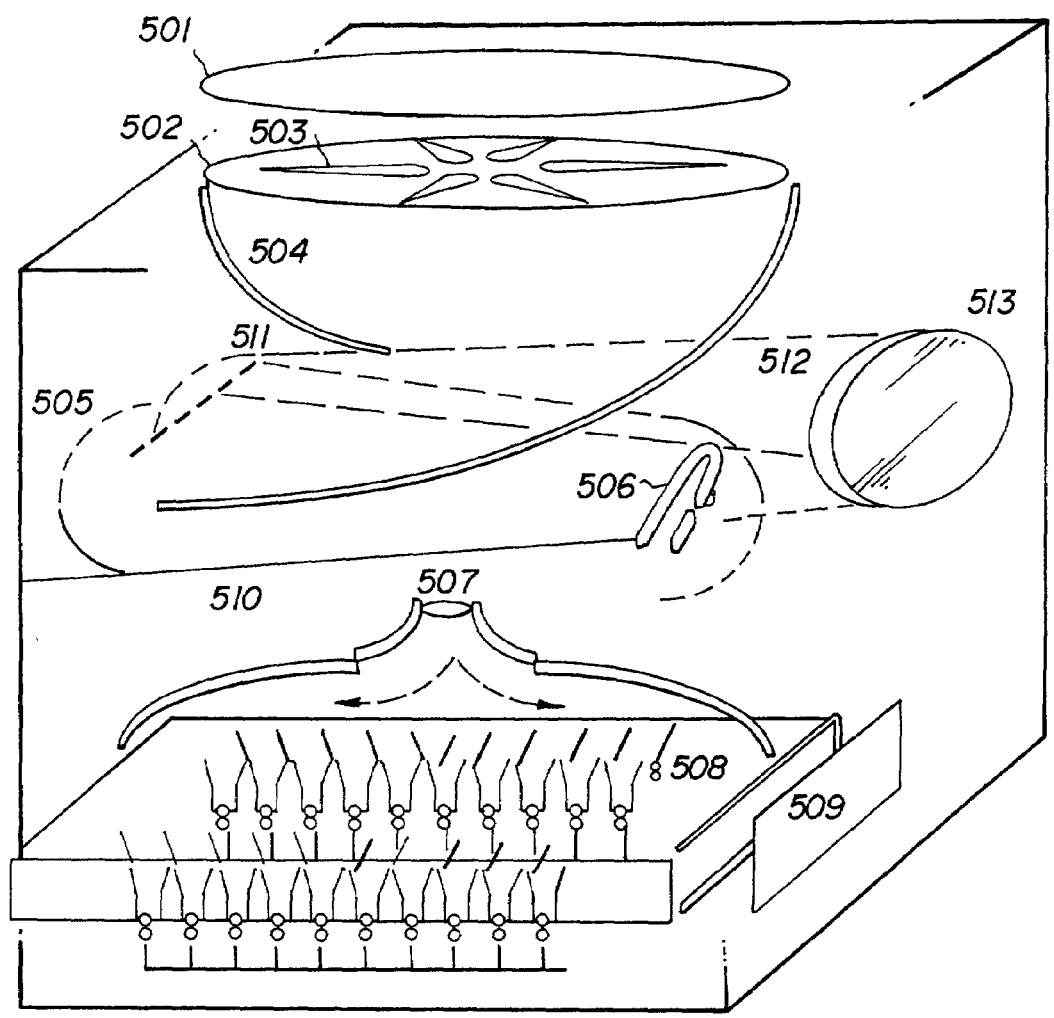
FIG. 5 discloses an alternative embodiment of the present invention.

To act omnidirectionally, the system can use four or more such intakes 300 disposed around a circle, and covered by a hat or cover 310, as shown in FIG. 3. These intakes 300 have a common (large-diameter) central opening 312, with a smooth transition to a common intake 314.

The main motive power for sampling is provided by a small DC-operated axial fan 320 moving approximately 15 L/m of air at very low pressure (pressure to be determined experimentally). This fan may be placed at the entrance or exit of the system.

The next subsystem concerns mechanical filtering. The entranceway 316 to these intakes 300 are covered by a mechanical dust filter 318 of high porosity. This filter 318 can be prepared using laser forming techniques and a hydrophobic base, available from Laserfare Inc. of Newport, R.I. . The design of the filter should be made to exclude particles of minimum diameter >10 mm with minimum back-pressure.

The mechanical filtering components generally act on the mechanical minimum diameter of a particle. In the region of interest here, the Reynolds Number Re<1 and the orientation of an elongated particle is random. However, the primary filtering method to eliminate, for example, dust and smoke, must therefore act on the aerodynamic (actually Stokes) diameter of the particle, and therefore mechanical filtering is insufficient.

Note that from elementary geometric considerations derived from close-packing theory, the maximum theoretical porosity of such a filter can be shown to approximate $$\frac{\pi}{2\sqrt{3}}.$$

Practical porosities of the order of 80% are therefore attainable, provided that a nonrandom filter-building process is utilized. A randomly generated filter (such as might be prepared chemically) has much lower porosity. The optimal design is that of the inversion of a hexagonal lattice in the X and Y dimensions (normal to the airflow) and a slightly bent tube in the Z direction. At the time of manufacturing, the laser-cut filters can be used to prepare molds for casting multiple copies, to reduce costs.

Because mechanical filtering alone is insufficient for desired system, the next subsystem concerns aerodynamic isokinetic filtering. Selection of particles having the desired aerodynamic diameters (as opposed to minimum diameters) is aerodynamic in nature. FIGS. **4*a*–4*c* illustrate the general dam mechanism as element 400*a*, 400*b*, and 400*c*. In FIG. 3, the fluid passes labyrinth 330 to pass over dams 340 for isokinetic filtering to collect particles of interest for impingement on the sensors of sensor array packages 350, which are preferably replaceable. Remaining fluid passes exit labyrinth 360 to exit/collection filter 370 and fan 320**.

The design of the isokinetic filter is somewhat counter-intuitive, involving dams **400*a*, 400*b*, or 400*c* at angles of attack (α) in the deep-stall region, i.e., greater than 90° in the preferred embodiment, but is borne out by research, analysis and computer simulation. In the regime of interest, aerosol particles having approximately the same density can be sorted by mean aerodynamic diameter quite efficiently. For the regions of interest, the diagram of FIGS. 4*a*–4*c*** are illustrative, and preliminary calculations have established the notional angle of attack of the aerodynamic filter.

In FIG. **4*a*, orifice 410*a* acquires particles of interest for impingement onto a surface. It is integrated into the dam 400*a* and is located on a backside (i.e., downstream side) thereof at a location appropriate for the desired isokinetic sorting. FIGS. 4*b* and 4*c* disclose similar embodiments. In FIG. 4*b*, a collection tube 420 is used to position an orifice 410*b* and in FIG. 4*c*, orifice 410*c* is positioned on the base 430 adjacent to the dam 400*c***.

The common aspect of all of these embodiments is that the orifice is at the downstream side of the dam or otherwise shielded from direct flow by the dam. Locating the orifice on the dam, on a separate collection tube, or on the base adjacent to the dam, but on the downstream side thereof, facilitates the isokinetic sorting. The ratio of stream velocity to orifice velocity, the angle of the dam, and the position and size of the orifice regulate the distribution of particles that enter the orifice. This is demonstrated in the simulation.

Although orifices **410*a* and 410*c* will generally be fixed, orifice 410*b* can optionally be easily repositioned by making collection tube 420 movable. For example, although there is no functional difference between an orifice 410*a* in the dam 400*a* and an orifice 410*b* on a collection tube 420 positioned to be shielded by the dam 400*b* from the prevailing flow vector, the angle of collecting tube 420 with respect to the base (i.e., X-axis) is also a solution variable. Sorting can be varied based on repositioning of the collection tube 420. Dam 400*c*** can also have utility as a trap door to cover a sensor.

Basically, as shown in FIG. 7, the dam 700 sets up a local vortex 710 which sorts the particles isokinetically, by density and aerodynamic diameter. The underlying theory is also discussed below, with preliminary analysis of the phenomenon, both extrapolated from experimental data and supported by a first-order simulation.

The final subsystem concerns impaction. After some analysis, the present inventors have concluded that the conventional aerodynamic impaction methodologies exhibited in commercial off-the-shelf viable-particle impactors are satisfactory and probably optimal for the present application. An existing impaction chamber design, such as those available from Anderson Instruments, 500 Technology Court, Smyrna, Ga. 30082, USA, is therefore usable for the present invention.

FIG. 5 illustrates an alternate embodiment of the invention in which such an impaction chamber 507 is employed. In this embodiment, large particles and rain are excluded by input rain and sun hat 501 and large particle filter 502. Fluid then passes through NACA fluid dynamic intake orifices 503 to a collector and second filter 504 to an intake labyrinth and venturi 505 that directs the fluid over fluid dynamic dam 506 which acts as an inertial filter to obtain particles of interest at an orifice at the rear. Particles of interest are directed by inertial impactor 507 (which can optionally be replaced with the electrodynamic impaction discussed above) over the open trap doors of sensors 508 which are optionally replaceable via drawer 509. The remaining fluid is collected in chamber 510, passed through exit labyrinth 511 to fan 512 to exit collector and filter 513.

The apparent particle density of an aerosol is generally much smaller than the actual density, with coefficients of sphericity (ratio of surface area of an equivalent sphere to actual surface area ($A/A_0$)). This means that for organic aerosols the apparent density is uniformly less than unity, and in the range where Stokes' Law does not apply experimentally very well. For the region of interest it amounts to a correction to Stokes' Law, and the inventors have chosen to use experimental data as guidance. Below, it is noted that preliminary simulation results using the assumptions underlying Stokes' Law are quantitatively consistent with the extrapolated experimental data. Robinson (see *Comm. Pure Applied Math,* 9,69) demonstrated that in these cases gravitational and inertial collection efficiencies are additive.

From the point of view of alveolar deposition (which is most critical from an infection viewpoint, and therefore defines both threat and measurement), the most recent data from Lippmann (see Lippmann, M. "Regional Deposition of Particles in the Human Respiratory Tract", in *Handbook of Physiology*, American Physiological Society, Bethesda, Md. 1977) suggests that for both oral and nasal alveolar deposition the optimum aerodynamic diameter is of the order of 1–5 μm, with tails of about 0.7–7 μm at the 15% efficiency level.

Without belaboring the derivation, from Stokes' Law and the assumptions of low Reynolds Number it can be shown that gravitational settling is fairly independent of wind velocity (including turbulence) and is given by $$Re^2 \varphi = \frac{8 * [(4/3)\pi r^3] \gamma_a \gamma g}{\pi \eta^2}$$

where Re is the Reynolds Number, which by definition=$2r\gamma_a V/\eta$ yielding the velocity V, and where
γ=density of the particle
$\gamma_\alpha$=density of the air
g=gravitational acceleration
η=viscosity of the air There are better approximations based on empirical data, but for this analysis and design purposes they can be ignored unless it is required to accurately measure particle density and mean radius.

Figure 6:
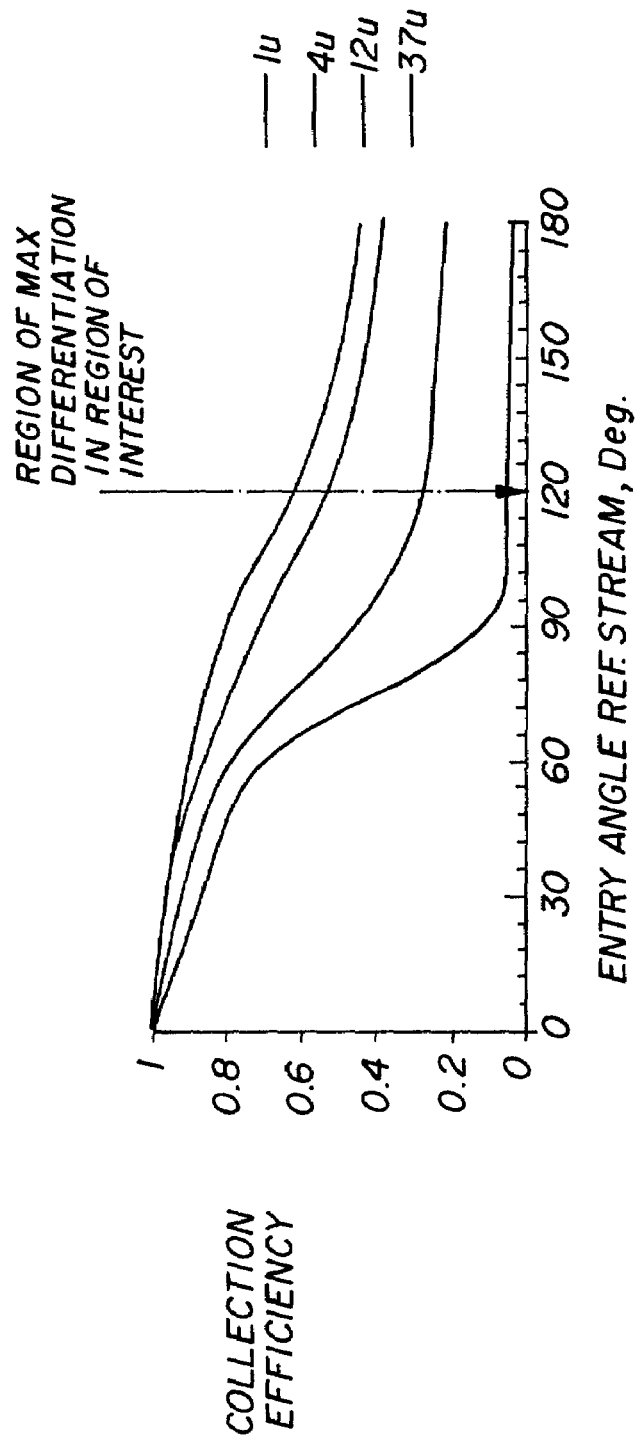
FIG. 6 discloses isokinetic flow model results for the present invention.

Data from Watson (see *Amer. Ind. Hyg. Ass. Quarterly*, 3,29) is shown in FIG. 6, which has been nondimensionlized (appropriate in the region of interest) has been extrapolated by the inventors to cover the expected particle size range ($\rho_{eff}$=1), indicating how the sorting mechanism will select out particles of the appropriate size. These data are fortunately nondimensional, and confirm the present design and analysis. Most importantly, smoke particles, having effective diameters well under 0.5 μm will be rejected.

For the aerodynamic sorting, the entire air-handling problem is properly modeled by the Navier-Stokes formulation.

$$\left[\frac{\partial u_i}{\partial t}\right] + \left[\frac{\partial u_i}{\partial x_j}\right] \cdot [u] =$$

$$-\frac{1}{\rho}\left[\frac{\partial p}{\partial x_j}\right] + \begin{bmatrix} 0 \\ 0 \\ -g \end{bmatrix} + \frac{\mu}{\rho}\left(\sum_j \left[\frac{\partial^2 u_i}{\partial x_j^2}\right] + \frac{1}{3}\left[\frac{\partial^2 u_j}{\partial x_i \partial x_j}\right]\right)$$

supplemented by the Equation of Continuity (incompressible flow in this case) and the thermodynamic relationship (generally adiabatic flow with γ≈1.5, but also negligible in this instance).

Figure 7:
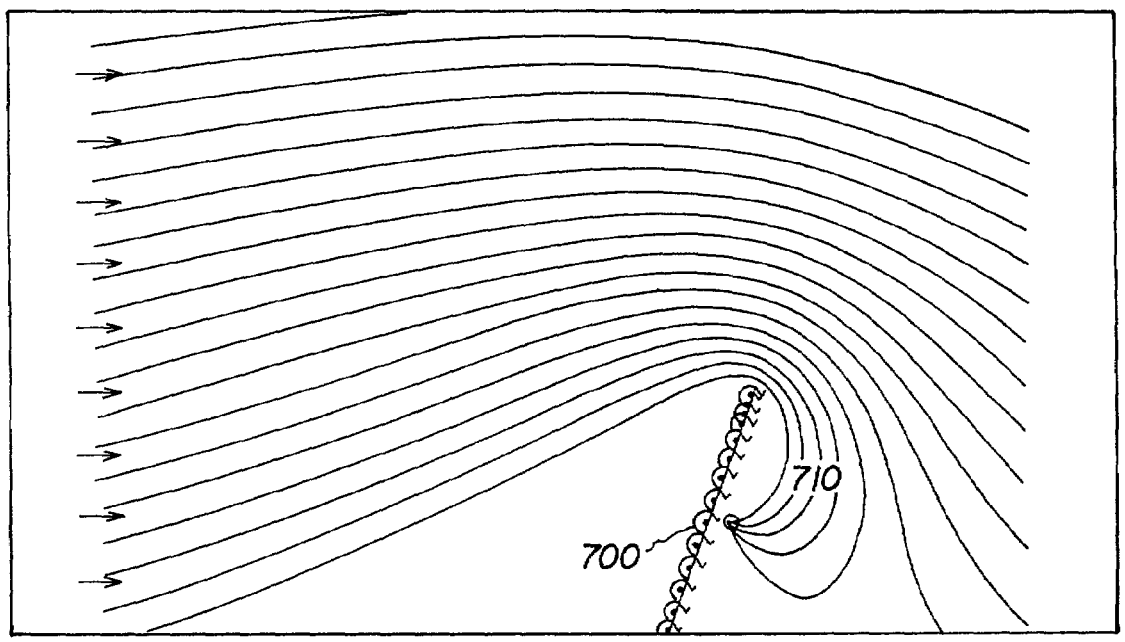
FIG. 7 discloses potential-based fluid flow mathematical simulation results for the aerodynamic sorting of the present invention.

Using a potential-based fluid flow simulator, available from the U. Mich. Department of Aerospace Engineering, a simple model of an appropriate obstruction to uniform flow was modeled at an appropriate angle. The results are illustrated in FIG. 7. Assumptions included incompressibility, and irrotational laminar flow. These assumptions are appropriate to the scenario including the prevailing Reynolds numbers (<<1). A number of runs were made, varying appropriate parameters (i.e., ratio of source to sink rates and angle of incidence), to demonstrate the aerodynamic filtering mechanism.

The airfoil angle of incidence in the pictured simulation was 210°. The non-dimensional input flow rate of the pictured simulation run was 1 sec$^{-1}$, and the sink rate was located at a notional fluid sink of 2 sec$^{-1}$ at the ventral center of an arbitrarily thin barrier. Other ratios of source to sink rate (1:1 to 1:3) provided similar results. The streamlines are shown. The equipotential lines are of course orthogonal to the streamlines, and reveal no surprises.

Our analysis has shown that the optimal incidence angle may vary from the incidence angle shown, including angles in the laminar, turbulent and stall regions, depending on the selection criteria, densities, velocities, and Reynolds numbers. Furthermore the collection orifice, while not directly in a streamline, may be partially so, located on the barrier, or on the substrate of the barrier, again depending on the conditions of design and operation. The class of inlets used for optimum pressure recovery, referred to as "NACA" or NACA-type" are generally unsuitable to this solution.

From these results, it is fairly obvious under the conditions in which Stokes' Law is valid (these being the case) that, to the first order, a particle of density p with a mean radius of r embedded in a much lighter fluid ($\rho_f<<\rho_p$) having a curved path with radius $r_a$ and a flow velocity of $v_a$ will have a terminal velocity component $v_p$ normal to the fluid streamlines (neglecting gravity, which can be vectorially added later) of:

$$v_p = \frac{4\rho r^2 v_a^2}{18 \mu r_a} = \kappa \frac{\rho r^2 v_a^2}{r_a}$$

which provides square-law sorting by particle size. Varying the incidence angle of course changes the flow and the local curvature of the streamlines, and the present invention anticipates an incidence angle of 180<α<270 (see simulation graphic) for particle sorting, and, from the simulation, for the stated conditions, α≅210 degrees seems optimal to provide the greatest dispersion of particle paths. Thus there is an approximate agreement between the extrapolated empirical data and the simulation.

The exact dam and entry angles can vary from those disclosed herein. (Note that 120° in the empirical diagram corresponds geometrically to an incidence angle of 210°.) This computational experiment merely serves (1) to demonstrate qualitatively the measured filtering effects and (2) provide a basis for detailed analytical simulation in the course of the project to optimize the aerodynamic sorting phase of the preferred embodiment of the present invention.

Figure 8:
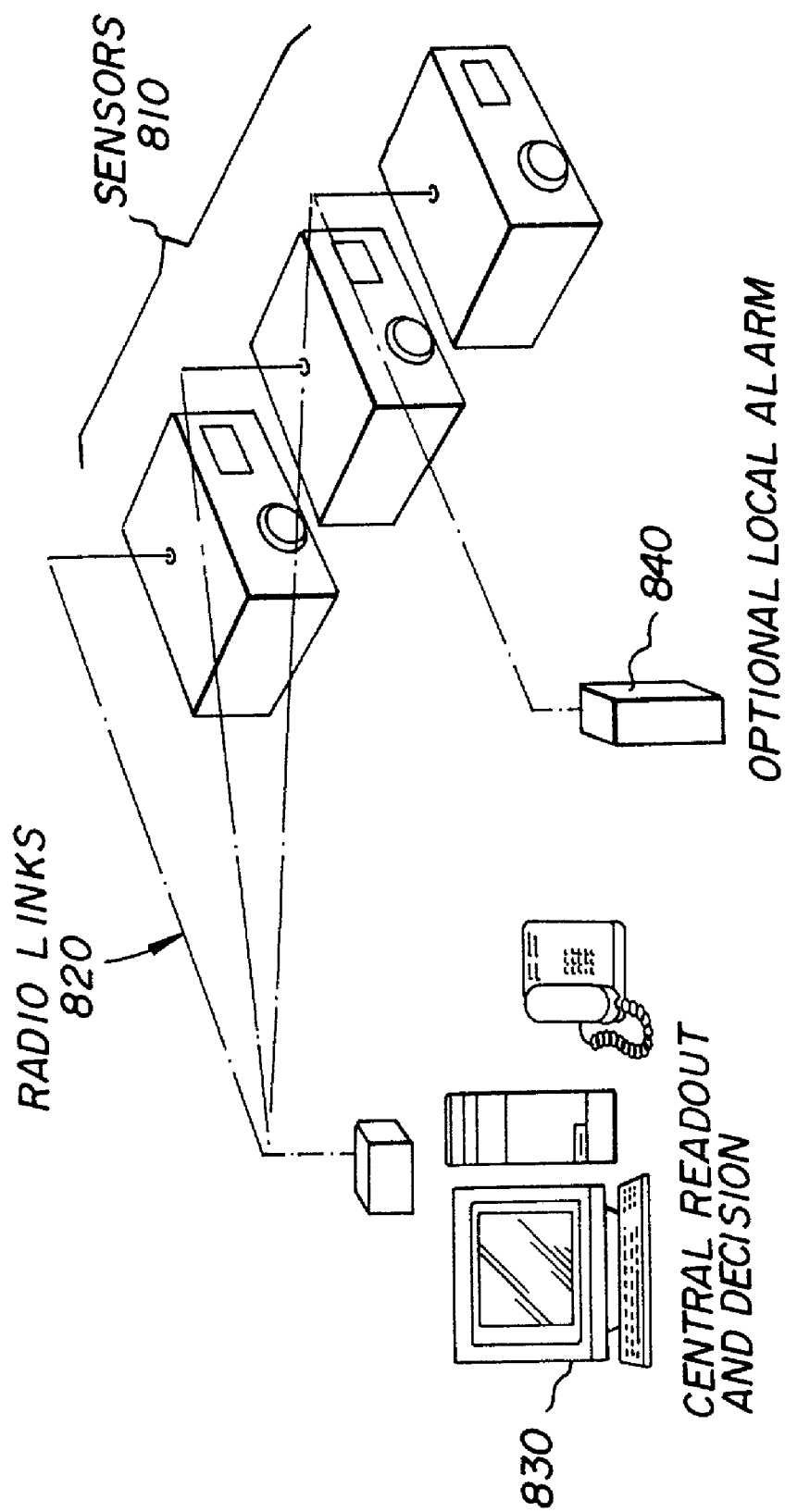
FIG. 8 discloses a typical deployment scenario of the present invention.

In use, the sensors of the present invention can be configured to be hand emplaceable, as shown in FIG. 8, or wearable (not shown). In a preferred embodiment, sensor units 810 are deployed and are linked, such as by radio links 820, to a central readout and decision center 830. If the sensor units 810 are deployed with military units or near populations, a local alarm 840 can be used to warn personnel.

An alternative deployment involves groups of individuals each carrying a wearable sensor sensitized for and optimized for a smaller class of agents. The aggregate wearable sensors in this group communicate locally among each other via low-powered radio signals, forming a self-organizing redundant network, to achieve a combination of selectivity and breadth of response. The aggregate results are then optionally communicated to the central readout and decision center.

The central readout and decision center 830 can (1) provide detection and classification of the agent, depending on the strength and signal time-characterizations reported by each well or container, and the pattern of responses among all the containers within the apparatus, (2) minimize both false negatives and false positives in the decision, (3) optionally deal with uncertainty or unanticipated patterns of response-including spoofing and obscuration-according to probabilistic rules, (4) compose an annunciation and diagnostic report message, and (5) transmit that message or annunciation by conventional means.

Although disclosed below with respect to aptamer-based bioreceptors, the same principles apply to nucleic acid, hybridized chemical and combinations thereof.

The general process of the present invention for using aptamer-based bioreceptors is analogous to that of the use of genetic algorithms to construct the desired sequences. The affinity of a putative aptamer to a target is determined by geometric as well as chemical considerations, being a mixture of folding properties, multipole electrostatic and van der Waals forces, generally both covalent and noncovalent bonds. The photonic conversion reporter process is a result of polarization changes in the sensor biomolecules.

A sensor aptamer of the present invention can be produced and deployed, for example, by the following method:
A. Develop targets of interest (e.g., JCS list agents, bacteria, pollens, viruses, prions, metabolic toxins, other pathogens, narcotic precursors and by-products, et cetera) by using infective and replication processes known in the literature;
B. Collect T-cell and B-cell populations where appropriate;
C. Prepare a large number of pseudorandom sequences of nucleic acids;
D. Mix them with the targets in solution phase;
E. Discard the unbound or weakly bound molecules, e.g., via electrophoretic or chromatographic methods;
F. Continue process of collecting adhering candidates, further modification through randomization and resorting proceeds until a desired degree of affinity is obtained;
G. Attach the photonic reporter molecules;
H. Attach the combined molecules to the substrate, typically glass or a decelularized biomembrane; and
I. Test and repeat.

This invention therefore provides for sensing biological, chemical or radiation challenges to humans, animals, and plants even when that challenge has not previously been catalogued, isolated and/or analyzed. It also can be used to reliably detect biological, chemical or radiation challenges to humans, animals and plants despite the presence of natural or deliberate mutations, and/or conformers, enantiomers and/or chimeric agents.

We claim:

1. A method of detecting the presence of chemicals, vira, and bacteria in air samples, comprising:

choosing a non-living bioreceptor consisting essentially of desired sensor molecules selected from the group consisting of aptamers, single-chain nucleic acids, double-chain nucleic acids, hybridized chemicals incorporating these molecules and combinations thereof that produce a change in electrical potential when binding to a desired agent selected from the group consisting of chemicals, vira, and bacteria;
treating said bioreceptor with fluorescent or luminescent dye to emit photons in response to said change in electrical potential;
capturing an air sample by drawing said sample through an intake;
mechanically and/or aerodynamically filtering the sample to remove particles>10 μm;
using a dam to set up a local vortex to isokinetically sort particles by density and aerodynamic diameter;
selecting and impacting particles from the sample within a selected size range on a surface of said bioreceptor to introduce said agent to said surface of said bioreceptor, thereby forming binding therebetween; and
detecting said photons emitted by said bioreceptor to indicate the presence of said agent.

2. The method of claim 1, wherein said bioreceptor is formed of desired sensor molecules on a suitable substrate.

3. The method of claim 1, wherein said selected size range is approximately 1–5 μm.

4. The method of claim 1, further comprising collection of impacted agents that have been detected by photon emission.

5. A method of collecting, sorting, concentrating and impinging particles on a surface of a non-living bioreceptor, comprising:

capturing an air sample by drawing it through an intake;
mechanically and/or aerodynamically filtering the sample to remove particles>10 μm;
using a dam to set up a local vortex to isokinetically sort particles by density and aerodynamioc diameter; and
selecting and impinging particles from said simple within a selected size range on a surface of said bioreceptor to introduce said agent to said surface of said bioreceptor, wherein said bioreceptor consists essentially of non-livingsensor molecules selected from the group consisting of aptamers, single-chain nucleic acids, double-chain nucleic acids, hybridized chemicals incorporating these molecules and combinations thereof that produce a change in electrical potential when binding to said agent.

6. The method of claim 5, further comprising providing a photocell, wherein said bioreceptor is treated with fluorescent or luminescent dye to emit photons in response to said change in electrical potential so as to detect said presence of said agent with said photocell.

7. The method of claim 5, wherein said selected size range is 0.7–7 μm.

8. The method of claim 5, wherein said selected size range is 1–5 μm.

9. The method of claim 5, wherein said dam has an angle of attack>90 degrees with respect to the direction of air flow of said air sample.

10. The method of claim 5, wherein said dam has an angle of attack beyond an aerodynamic stall angle of said agent in said air sample.

11. An apparatus for biosensing an agent by collecting, sorting, concentrating and impinging particles on a surface of a non-living bioreceptor, comprising:
- means for capturing a an air sample by drawing it through an intake;
- means for mechanically and/or aerodynamically filtering the sample to remove particles>10 μm;
- means to set up a local vortex with a dam to isokinetically sort particles by density and aerodynamic diameter; and
- means for selecting and impinging particles within a selected size range on a surface of said bioreceptor to introduce said agent to said surface of said bioreceptor, wherein said surface is disposed within the apparatus and said bioreceptor consists essentially of non-living sensor molecules selected from the group consisting of aptamers, single-chain nucleic acids, double-chain nucleic acids, hybridized chemicals incorporating these molecules and combinations thereof that produce a change in electrical potential when binding to said agent.

* * * * *